United States Patent [19]

Bazinet et al.

[11] Patent Number: 5,177,000
[45] Date of Patent: * Jan. 5, 1993

[54] MONOCLONAL ANTIBODIES SELECTIVE FOR PROSTATE CANCER AND DIAGNOSTIC IMMUNOASSAY FOR PROSTATE CANCER

[75] Inventors: Michel Bazinet; Richard J. Cote; Lloyd J. Old, all of New York, N.Y.

[73] Assignee: Sloan Kettering Institute for Cancer Research, New York, N.Y.

[*] Notice: The portion of the term of this patent subsequent to Nov. 13, 2007 has been disclaimed.

[21] Appl. No.: 573,398

[22] Filed: Aug. 24, 1990

Related U.S. Application Data

[63] Continuation of Ser. No. 881,630, Jul. 3, 1986, Pat. No. 4,970,299.

[51] Int. Cl.⁵ .................. G01N 33/53; C07K 15/28; C12N 5/20
[52] U.S. Cl. .................. 435/7.23; 530/388.8; 530/389.7; 530/391.3; 435/240.27; 435/172.2; 435/70.21
[58] Field of Search ........... 530/387, 388, 388.8, 530/391.3, 389.7; 435/240.27, 7.23

[56] References Cited

PUBLICATIONS

Frankel et al. PNAS 79: 903-907, 1982.
Houghton et al. Seminars in Oncology 13(2): 165-179, Jun. 1986.

Primary Examiner—David L. Lacey
Assistant Examiner—Paula Hutzell
Attorney, Agent, or Firm—John P. White

[57] ABSTRACT

Four monoclonal antibodies are found which selectively identify prostate cancer. These monoclonals are therefore useful in diagnosis and differential diagnosis of prostate cancer.

3 Claims, No Drawings

MONOCLONAL ANTIBODIES SELECTIVE FOR PROSTATE CANCER AND DIAGNOSTIC IMMUNOASSAY FOR PROSTATE CANCER

The invention was made in part with government support under CA 08748 awarded by the National Cancer Institute. The government has certain rights in this invention.

This is a continuation of application Ser. No. 881,630, filed Jul. 3, 1986, now U.S. Pat. No. 4,970,299.

The present invention relates to a method of using monoclonal antibodies and their antigenic specificities in identifying, characterizing as well as determining a prognosis for human prostate cancers. This is a useful diagnostic tool in the detection, clinical prognosis and therapy of prostate cancer as well as the study of the nature of prostate cancer. Antigenic profiles offer insight into prognosis for prostate cancer types.

Red blood cells, immunoflorescent, radioactive or enzymatic tagging agents can be bound to the highly specific antibodies using normal procedures, as required for indexing methods. Cytotoxic or cytostatic agents can also be bound to the highly specific antibodies to produce so called "magic bullet" type therapeutic agents which selectively destroy the cells with which the specific antibody binds.

DESCRIPTION

In 1975 Köhler and Milstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Kohler-Millstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteins that have the ability to combine with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man and is relatively advanced. (See U.S. Pat. Nos. 4,361,549-550; 4,364,932-37 and 4,363,799 concerning mAb to Human T-cell antigens). Little is known about differentiation antigens displayed oh normal and neoplastic cells belonging to other lineages especially prostate.

This is due to the difficulty of obtaining a ready source of the appropriate normal or tumor cell type as well as the vagaries of the art of monoclonal antibodies. The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining surface antigens on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens.

The analysis of cell surface antigens of human malignant melanoma was identified by mouse monoclonal antibodies (mAbs) (Dippold et al. Proc. Natl. Acad. Sci. USA 77, 6114–6118 (1980)). Previous work on $S_{27}$ in renal cancer is found in a co-pending patent application Ser. No. 277,814 Monoclonal Antibodies To Cell Surface Antigens of Human Renal Cancer and Ser. No. 474,224 Monoclonal Antibodies to Human Renal Cancer Antigens and Method hereby incorporated by reference.

Co-pending U.S. patent application Ser. No. 297,814, now U.S. Pat. No. 4,650,756 (Dippold, et al Proc. Natl. Acad. Sci. USA 77, 6614–6118 (1980)), has generated a series of mouse Abs that defined 12 new systems of human cell surface antigens. Six of these had been identified as glycoproteins (gp95, gp150, gp160, gp120r, gp120nr, and gp115), three are heat-labile antigens that could not be immunoprecipitated from labeled cell extracts ($S_{25}$, $M_{19}$, and $R_8$), and three are heat-stable antigens, presumably glycolipids ($O_5$, $R_{24}$, and $V_1$).

The monoclonal antibody technology is being applied to many areas of oncology. Mouse monoclonal antibodies (mAb) are currently being used in the immunohistological diagnosis and classification of tumors and in tumor localization and therapy.

Several laboratories have generated mAbs that recognize antigens associated with prostatic tissues including several which appear to be prostate-specific. However, most of these antibodies react with antigens expressed by both benign and malignant prostatic tissues. In order to facilitate the diagnosis and further characterize the progression of this malignancy, it would be of interest to define markers which distinguish benign from malignant prostatic tissues.

We report here on the initial analysis and distribution of four mAbs reactive with prostate cancer.

MATERIALS AND METHODS

Three mAbs - P25.15 (IgG$_1$), P25.48 (IgG$_3$) and P25.91 (IgG$_{2a}$) - were derived from a fusion using fresh prostate cancer (P251) as the immunogen. The mouse splenocytes were fused with the NS-1 mouse myeloma using standard Kohler-Milstein techniques. The initial screening of hybrid supernatants were performed on frozen sections of the tumor P251 using indirect immunofluorescence (IIF) by methods known in the art. Positive clones were subcloned three times by limiting dilution. Further analysis on different prostatic tissues was performed by IIF and/or indirect immunoperoxidase (IIP) staining of frozen tissue sections using the avidin-biotin immunoperoxidase system (Vector Laboratories). The analysis on non-prostatic tissues were performed exclusively by IIP.

S27 (IgG$_1$) is a well-characterized mAb initially developed in our laboratory against renal cancer that has been shown to react with prostate (Finstad et al. Proc. Nat'l. Acad. Sci. USA 1985; 82:2955). It has been shown to recognize the adenosine deaminase-binding protein (gp120). SK-RC-7 is the immunogen cell line leading to mAb S27. TURP-27 (IgG$_3$) developed by Wright et al (Cancer Res. 1986: 46:367) detects an antigen expressed by benign and malignant prostatic epithelium but not by most normal tissues. Hybridoma culture supernatants of S27 and TURP-27 were used for IIF and IIP analysis as described above.

S27 has been deposited at the Sloan-Kettering Institute, 1275 York Avenue, New York, N.Y. 10021 and at the American Type Culture Collection (ATCC), 12301 Parklawn Drive, Rockville, Md. 20852 on Nov. 15, 1983, has the ATCC designation HB 8428 and is a deposit under the Budapest Treaty.

P25.48, P25.91 and P25.15 are on deposit at Sloan-Kettering and at the ATCC under the designations below.

| Monoclonal Antibody | ATCC No. |
|---|---|
| P25.15 | HB 9140 |
| P25.48 | HB 9119 |
| P25.91 | HB 9120 |

TABLE I

INDIRECT IMMUNOFLUORESCENCE AND IMMUNOPEROXIDASE ANALYSIS OF FROZEN SECTIONS OF PROSTATIC TISSUES

| SPECIMENS | P25.48 IgG$_3$ | P25.91 IgG$_{2a}$ | P25.15 IgG$_1$ | S27 IgG$_1$ |
|---|---|---|---|---|
| NORMAL | | | | |
| P121 | − | − | − | − |
| P211 | − | − | + | + +(b) |
| BPH | | | | |
| P61 | − | − | + | + + |
| P111 | − | − | − | + + |
| P141 | − | − | − | + + |
| P151 | − | − | − | + + |
| P181 | − | − | − | + + |
| P191 | − | − | | |
| P261 | − | − | | |
| P341 | − | − | + +(b) | + + |
| P391 | − | − | + | − −(b) |
| P671 | −(a) | − | | |
| P681 | − | − | | |
| P721 | −(a) | −(a) | | |
| P781 | − | − | | |
| CARCINOMA | | | | |
| Well-Differentiated | | | | |
| P321 | − | − | − + | − −(b) |
| P551 | | | − | − − |
| P831 | − | − | | |
| Moderately Well-Differentiated | | | | |
| P101 | − | − | − | − + |
| P301 | − + | − − | − − | − +(b) |
| P351 | − | − | + − | + +(b) |
| P361 | − | − | − | + −(b) |
| P531 | − +(b) | − −(b) | + −(b) | − − |
| P541 | + +(b) | + +(b) | + − | + +(b) |
| Moderately to Poorly Differentiated | | | | |
| P251 | + + | − − | − − | + + |
| P441 | + +(b) | − +(b) | + + | + +(b) |
| Poorly or Undifferentiated | | | | |
| P461 | − | − | + | + +(b) |
| P501 | − | − | − | − |
| P651 | − − | − | | |

− NO REACTIVITY
− WEAK REACTIVITY
− − STRONG REACTIVITY
(a)Epithelium negative but some glands contained positive secretions
(b)Heterogenous reactivity

TABLE II

INDIRECT IMMUNOPEROXIDASE ANALYSIS OF FROZEN SECTIONS OF NON PROSTATIC TISSUES

| | # | P25.48 IgG$_3$ | P25.91 IgG$_{2a}$ | # | P25.15 IgG$_1$ | S27 IgG$_1$ |
|---|---|---|---|---|---|---|
| NORMAL TISSUES | | | | | | |
| Lung | (3) | − | − | (2) | ½ | − |
| Bronchus | (1) | − | − | (1) | − − | − |
| Liver | (2) | − | ½ | (1) | − − | − |
| Stomach | (3) | − | − | (2) | − | −(c) |
| Jejunum | (1) | − | − | (1) | − | + − |
| Colon | (3) | − | − | (2) | − | −(c) |
| Salivary | (2) | − | − | (1) | − − | − − |
| Pancreas | (2) | − | − | (2) | − −/− | − |
| Throid | (1) | − | − | (1) | − | − |
| Adrenal | (2) | − | − | (1) | − | − |
| Kidney | (3) | − | ⅓(b) | (1) | − | − − |
| Ureter | (1) | − | − − | | | |
| Bladder | (1) | − | − | (1) | + − | − |
| Seminal Vesicule | (2) | − | − | (2) | ½ | ½ |
| Vas Deferens | (1) | − | − | (1) | − | − − |
| Testis | (1) | − | − | | | |
| Atrophic Ovary | (1) | − | − | | | |
| Fallopian Tube | (1) | − | − | | | |
| Uterine Cervix | (1) | −(c) | − | | | |
| Breast | (2) | ½(d) | ½(d) | | | |
| Skin | (1) | − | − | (1) | − | − |
| MALIGNANT TISSUES | | | | | | |
| Lung | (1) | − | − | | | |
| Breast | (3) | − | − | | | |
| Stomach | (1) | − | − | | | |
| Salivary | (1) | − | − | | | |
| Kidney | (1) | − | − | | | |
| Bladder | (1) | − | − | | | |
| Seminoma | (1) | − | − | | | |
| Melanoma | (2) | − | − | | | |

− NO REACTIVITY
− WEAK REACTIVITY
− − STRONG REACTIVITY
(a)Although clearly negative on epithelial cells, P25.91 is weakly reactive with the stroma in 60% of the specimens tested
(b)Weak reactivity with the proximal tubule
(c)Epithelium negative but stroma showed weak reactivity
(d)Some ducts showed strong reactivity.

We see therefore from Tables I and II that P25.48 and P25.91 appear to distinguish benign from malignant prostatic epithelium. They react with a subset of prostatic cancers (7/13) but do not react with benign prostatic epithelium (0/15).

The antigens recognized by P25.48 and P25.91 show a very restricted distribution on normal and malignant non-prostatic tissues (Table II).

P25.15 and S27 react with most benign and malignant prostatic tissues. The reactivity of S27 on malignant prostatic tissues is frequently heterogenous, although it is usually homogeneous on benign epithelium. S27 and P25.15 were found to react with a subset of normal tissues. They were found to react with most prostate tissues tested, including benign prostates and prostate cancers.

The antigens recognized by P25.15 and S27 show moderate degree of restriction for normal tissues.

These antibodies are therefore useful for the diagnosis, subclassification, imaging and therapy of prostatic cancer.

For imaging monoclonal antibody can be linked or bound to a radioactive or fluorescent substance. For diagnosis antigen-antibody complex can be detected or visualized by methods known in the art such as Mixed hemabsorption assay, rosetting, immunofluorescence, immunoperoxidase etc. For therapy, monoclonal antibody can be linked to a radioactive label or a drug or therapeutic material, poisen or cryotoxic agent to help kill the cancer cells bound by the monoclonal antibody.

This invention also provides a kit for the diagnosis, differential diagnosis and treatment of prostate cancer comprising in package form one or more of the monoclonal antibodies selected from the group consisting of $S_{27}$, P25.15, P25.48, and P25.91.

What is claimed:

1. A panel of monoclonal antibodies consisting essentially of the monoclonal antibody P25.48 (ATCC No. HB 9189), the monoclonal antibody P25.91 (ATCC No. HB 9120), and the monoclonal antibody P25.15 (ATCC Accession No. HB 9140) labelled with detectable markers.

2. A method of diagnosing prostate cancer by immunohistological staining of prostate tissues using monoclonal antibody P25.48 produced by the hybridoma cell line ATCC 9119.

3. A method of diagnosing prostate cancer by immunohistological staining of prostate tissues using monoclonal antibody P25.48 produced by the hybridoma cell line ATCC 9120.

* * * * *

UNITED STATES PATENT AND TRADEMARK OFFICE
CERTIFICATE OF CORRECTION

PATENT NO. : 5,177,000
DATED : January 5, 1993
INVENTOR(S) : Michel Bazinet, Richard J. Cote, and Lloyd J. Old It is certified that error appears in the above-identified patent and that said Letters Patent is hereby corrected as shown below:

In column 2, line 11; "displayed oh," should read --displayed on--.

In column 4, line 37. "Long," should read --Lung--.

In column 4, line 44; "Throid," should read --Thyroid--.

In column 6, line 14, "HB 9189," should read --HB 9119--.

In column 6, line 24, "P25.48," should read --P25.91--.

Signed and Sealed this

Fourteenth Day of June, 1994

Attest:

BRUCE LEHMAN

*Attesting Officer*        Commissioner of Patents and Trademarks